United States Patent [19]

Guadagno

[11] Patent Number: 5,702,913
[45] Date of Patent: Dec. 30, 1997

[54] CHROMGEN-REAGENT TEST SYSTEM

[75] Inventor: Philip A. Guadagno, Vidor, Tex.

[73] Assignee: Helena Laboratories Corporation, Beaumont, Tex.

[21] Appl. No.: 364,525

[22] Filed: Jun. 12, 1989

Related U.S. Application Data

[63] Continuation of Ser. No. 563,903, Dec. 21, 1983, abandoned.

[51] Int. Cl.$^6$ .................... G01N 21/00; G01N 33/72; C12Q 1/28; C12N 9/99
[52] U.S. Cl. .................... 435/28; 422/56; 422/61; 435/28; 435/184; 435/810; 436/66; 436/169
[58] Field of Search .................... 435/28, 184, 810; 436/66, 169; 422/56, 61

[56] References Cited

U.S. PATENT DOCUMENTS

| | | |
|---|---|---|
| Re. 28,575 | 10/1975 | Bauer . |
| 2,223,520 | 12/1940 | Ioannu . |
| 2,290,436 | 7/1942 | Kamlet . |
| 2,387,244 | 10/1945 | Compton et al. . |
| 2,394,140 | 2/1946 | Biscow . |
| 2,418,392 | 4/1947 | Bender . |
| 2,567,445 | 9/1951 | Parker . |
| 2,754,289 | 7/1956 | Meyer . |
| 2,773,906 | 12/1956 | Emerson . |
| 2,799,660 | 7/1957 | Nicholls et al. . |
| 2,800,457 | 7/1957 | Green et al. . |
| 2,800,458 | 7/1957 | Green . |
| 2,823,984 | 2/1958 | Mavrodineanu . |
| 2,838,377 | 6/1958 | Fonner . |
| 2,848,308 | 8/1958 | Free . |
| 2,886,445 | 5/1959 | Rosenthal et al. . |
| 2,893,844 | 7/1959 | Cook . |
| 2,905,594 | 9/1959 | Morris . |
| 2,930,695 | 3/1960 | Rosner et al. . |
| 2,953,454 | 9/1960 | Berman . |
| 2,986,453 | 5/1961 | Collins . |
| 3,012,976 | 12/1961 | Adams, Jr. et al. . |
| 3,017,879 | 1/1962 | Sapit et al. . |
| 3,034,922 | 5/1962 | Böe et al. . |
| 3,042,496 | 7/1962 | Fancher et al. . |
| 3,043,782 | 7/1962 | Jensen . |
| 3,057,723 | 10/1962 | Jeffreys et al. . |
| 3,066,081 | 11/1962 | Rorem et al. . |
| 3,092,463 | 6/1963 | Adams, Jr. et al. . |
| 3,092,464 | 6/1963 | Adams, Jr. et al. . |
| 3,116,223 | 12/1963 | Rosner et al. . |
| 3,183,173 | 5/1965 | Oakes . |
| 3,232,710 | 2/1966 | Rieckmann et al. . |
| 3,252,762 | 5/1966 | Adams, Jr. et al. . |
| 3,290,117 | 12/1966 | Adams, Jr. et al. . |
| 3,293,683 | 12/1966 | Wyant . |
| 3,350,278 | 10/1967 | Gretton et al. . |
| 3,406,015 | 10/1968 | Foster . |
| 3,406,106 | 10/1968 | Garwood et al. . |
| 3,411,887 | 11/1968 | Chiu-Choon Ku . |
| 3,418,079 | 12/1968 | Rey et al. . |
| 3,438,737 | 4/1969 | Atkinson et al. . |
| 3,443,903 | 5/1969 | Haack et al. . |
| 3,447,536 | 6/1969 | Snyder . |
| 3,453,180 | 7/1969 | Fraser, Jr. et al. . |
| 3,466,145 | 9/1969 | Duyne . |
| 3,472,738 | 10/1969 | Foster . |
| 3,507,269 | 4/1970 | Berry . |
| 3,509,872 | 5/1970 | Truhan . |
| 3,511,608 | 5/1970 | Anderson . |
| 3,526,480 | 9/1970 | Findl et al. . |
| 3,552,925 | 1/1971 | Fetter . |
| 3,558,435 | 1/1971 | Rey et al. . |
| 3,598,704 | 8/1971 | Dablqvist . |
| 3,625,654 | 12/1971 | Duyne . |
| 3,627,697 | 12/1971 | Rey et al. . |
| 3,627,698 | 12/1971 | Rey et al. . |
| 3,630,847 | 12/1971 | Rey et al. . |
| 3,630,957 | 12/1971 | Rey et al. . |
| 3,654,179 | 4/1972 | Bauer . |
| 3,654,180 | 4/1972 | Bauer . |
| 3,668,076 | 6/1972 | Rey et al. . |
| 3,672,351 | 6/1972 | Ubersax et al. . |
| 3,699,005 | 10/1972 | Foster . |
| 3,712,853 | 1/1973 | Rittersdorf et al. . |
| 3,713,772 | 1/1973 | Tavel . |
| 3,811,840 | 5/1974 | Bauer et al. . |
| 3,814,668 | 6/1974 | Blake et al. . |
| 3,847,553 | 11/1974 | Verbeck . |
| 3,853,468 | 12/1974 | Haymond . |
| 3,853,471 | 12/1974 | Rittersdorf et al. . |
| 3,853,472 | 12/1974 | Rittersdorf et al. . |

(List continued on next page.)

FOREIGN PATENT DOCUMENTS

| | | |
|---|---|---|
| 093595 | 11/1983 | European Pat. Off. . |
| 0047359 | 2/1972 | Japan . |
| 1018563 | 1/1966 | United Kingdom . |

OTHER PUBLICATIONS

Wood et al—The Dispensatory of the U.S. of America—23rd edition (1943) pp. 507–508.
Heinrich et al., Klin Wochenschr 58(23): 1283–1298 (1980).

*Primary Examiner*—James C. Housel
*Assistant Examiner*—Scott F. Welch
*Attorney, Agent, or Firm*—Dorsey & Whitney

[57] ABSTRACT

An improved chromogen-reagent test system for a slide, test kit or the like has particular utility in the testing of fecal specimens for occult blood. The chromogen-reagent system may include the use of colorless guaiac which, in the presence of a developing solution and a catalyst, is oxidized to yield a predetermined color such as blue. Hydrogen peroxide is used as the developing solution and hemoglobin in the fecal specimen functions as the catalyst. The chromogen-reagent test system includes an indicator area for determining if the guaiac and the developing solution are functioning properly, i.e., the test system of the present invention verifies that the guaiac has not lost its activity nor been improperly catalyzed and that the hydrogen peroxide has not lost its activity. The indicator area includes a catalyst which has a greater stability than blood, in respect to adverse environmental conditions, such that a determination can be made if the reagents are functioning properly.

11 Claims, 1 Drawing Sheet

U.S. PATENT DOCUMENTS

| | | |
|---|---|---|
| 3,854,885 | 12/1974 | Fromm et al. . |
| 3,912,457 | 10/1975 | Ogawa et al. . |
| 3,917,452 | 11/1975 | Rittersdorf et al. . |
| 3,964,871 | 6/1976 | Hochstrasser . |
| 3,975,161 | 8/1976 | Svoboda et al. . |
| 3,986,833 | 10/1976 | Mast et al. . |
| 3,996,006 | 12/1976 | Pagano . |
| 4,005,984 | 2/1977 | Alsop . |
| 4,017,261 | 4/1977 | Svoboda et al. . |
| 4,035,150 | 7/1977 | Jaffe . |
| 4,046,514 | 9/1977 | Johnston et al. . |
| 4,061,468 | 12/1977 | Lange et al. . |
| 4,063,894 | 12/1977 | Ogawa et al. . |
| 4,071,318 | 1/1978 | Lam . |
| 4,092,120 | 5/1978 | Suovaniemi et al. . |
| 4,148,611 | 4/1979 | Nand et al. . |
| 4,175,923 | 11/1979 | Friend .......................................... 436/66 |
| 4,219,336 | 8/1980 | Guthlein et al. . |
| 4,220,713 | 9/1980 | Rittersdorf et al. . |
| 4,251,222 | 2/1981 | White . |
| 4,251,223 | 2/1981 | White . |
| 4,260,393 | 4/1981 | Gibson . |
| 4,269,938 | 5/1981 | Frank . |
| 4,277,250 | 7/1981 | Melnick et al. . |
| 4,278,439 | 7/1981 | White . |
| 4,292,272 | 9/1981 | Kitajima et al. . |
| 4,303,409 | 12/1981 | Ogawa et al. . |
| 4,310,626 | 1/1982 | Burkhardt et al. . |
| 4,329,317 | 5/1982 | Detweiler et al. . |
| 4,333,734 | 6/1982 | Fleisher ...................... 436/66 |
| 4,365,970 | 12/1982 | Lawrence et al. .......... 422/56 |
| 4,385,114 | 5/1983 | Güthlein et al. . |
| 4,447,542 | 5/1984 | Gantzer . |
| 4,486,536 | 12/1984 | Baker et al. ................ 436/66 |
| 4,493,892 | 1/1985 | Fleisher ...................... 435/28 |
| 4,511,533 | 4/1985 | Guadagno et al. . |
| 4,541,987 | 9/1985 | Guadagno ................... 422/56 |
| 4,556,640 | 12/1985 | Gantzer . |
| 4,578,358 | 3/1986 | Oksman et al. . |
| 4,725,553 | 2/1988 | Guadagno . |
| 4,742,002 | 5/1988 | Guadagno . |

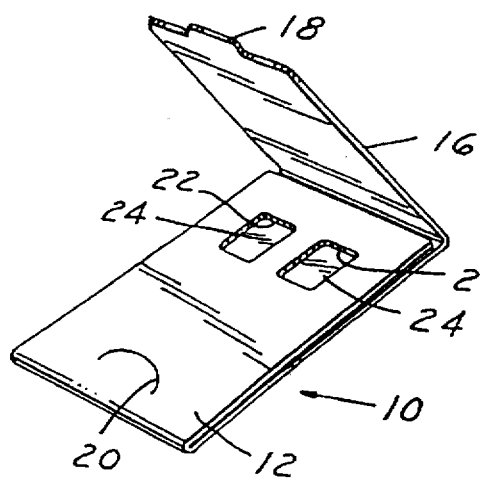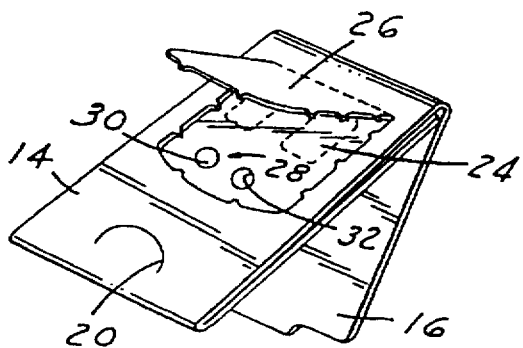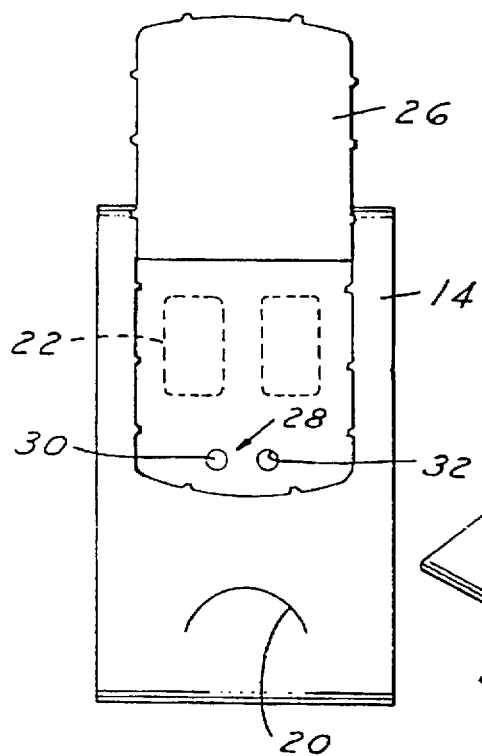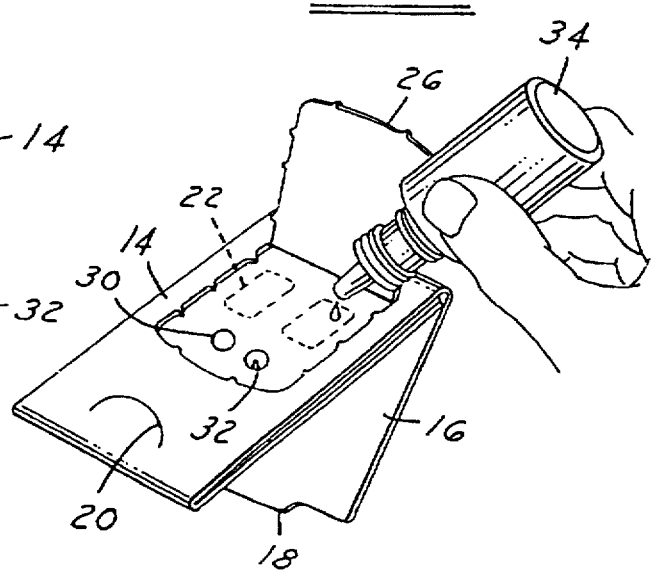

CHROMGEN-REAGENT TEST SYSTEM

This is a continuation of application Ser. No. 06/563,903, filed Dec. 21st, 1983 now abandoned.

BACKGROUND OF THE INVENTION

This invention relates generally to chromogen-reagent test systems for use with test kits, test slides or the like. The present invention has a particular utility in connection with kits or slides used in testing fetal specimens for occult blood and hence the present invention will be explained in that context.

Specimen test slides and procedures for detecting fecal occult blood are well known. Two such systems are described in Pagano U.S. Pat. No. 3,996,006 and Friend U.S. Pat. No. 4,175,923, respectively.

Recently, U.S. Pat. No. 4,365,970 issued to Lawrence et al on Dec. 28, 1982. The Lawrence et al patent describes certain problems which may occur in testing fecal specimens for occult blood utilizing specimen test slides. To understand the problems as presented in the Lawrence et al patent, an explanation of the test procedure for fetal occult blood will be helpful.

One test for fecal occult blood is a hemoglobin catalyzed oxidation of a reagent such as guaiac with the guaiac functioning as a chromogen. The guaiac changes from colorless to blue as the oxidation takes place.

When a test slide is used, a substrate or specimen receiving sheet is impregnated or printed with guaiac. After the specimen is placed on the sheet, a developing solution such as hydrogen peroxide is applied to the sheet in the area of the specimen. If the blood is present in the fecal specimen, the blood will catalyze the liberation of oxygen from the hydrogen peroxide and the liberated oxygen will oxidze the guaiac. Oxidation of the guaiac will cause the guaiac impregnated paper to turn blue in the area of the specimens.

As explained in the Lawrence et al U.S. Pat. No. 4,365,970 a disadvantage associated with the aforementioned test is that false positive and false negative test results may occur. Specifically, the Lawrence et al patent, at column 1 lines 38 et seq states that "Any condition such as exposure of the slide to heat or sunlight could cause loss of activity of either the guaiac or the hemoglobin . . . and could result in a false negative test. Alternatively, exposure of the slide to traces of metals such as copper or iron which are also guaiac catalysts could lead to false positive test."

The Lawrence et al patent discloses, as a solution to the aforementioned problem, the provision of a control area 34 on the test slide, with positive and negative monitors 34a, 34b. According to the Lawrence et al patent, the positive area should employ either hemoglobin or a catalyst which would react to adverse environmental conditions in a manner similar to hemoglobin. (See Lawrence et al patent, column 4, lines 3–6.) The negative area is a defined region of the guaiac impregnated paper which will not provide a color change unless a catalyst other than hemoglobin is present.

The reason that the positive monitor of the Lawrence et al patent must either be hemoglobin or a substance which reacts to adverse environmental conditions in a manner similar to hemoglobin, is based on Lawrence et al's hypothesis that certain exposure . . . could cause loss of activity of . . . the hemoglobin. Thus if the "exposure"causes loss of activity of the hemoglobin in the specimen, such "exposure" should also cause loss of activity of the positive monitor in Lawrence et al.

The present invention is based upon the discovery that it is not necessary for the positive monitor to be either hemoglobin or a substance which reacts to adverse environmental conditions in a manner similar to hemoglobin, because it is not even necessary to test for loss of activity of the hemoglobin in the specimen due to "exposure"to the environment. The present invention is based upon the discovery that such a limitation as to the substance used for the positive monitor is both unduly restrictive and unnecessary.

Hence the present invention includes a recognition that it is only necessary to make a determination that the reagents are functioning properly in the test system, specifically in the case of the guaiac based test, that the guaiac and hydrogen peroxide are functioning properly.

SUMMARY OF THE INVENTION

The present invention relates to a chromogen-reagent test system where the test system is for verifying the efficacy or proper functioning of the reagents.

The present invention includes, at least in part, the discovery that contrary to the aforementioned Lawrence et al patent, it is not necessary that the positive monitor react to adverse environmental conditions in a manner similar to hemoglobin, since it is only necessary to test that the reagents are functioning properly.

BRIEF DESCRIPTION OF THE DRAWINGS

The various objects, benefits and advantages of the present invention will become more apparent upon reading the following detailed description of the invention taken in conjunction with the drawings.

In the drawings, wherein like reference numerals identify corresponding components:

FIG. 1 is a perspective view of one form of a fecal occult specimen slide illustrated from the front of the slide;

FIG. 2 is a perspective view of the fecal occult specimen slide of FIG. 1 as viewed from the rear showing the area for testing the reagents;

FIG. 3 is an enlarged rear elevational view of the slide of FIG. 1; and

FIG. 4 is a perspective illustration of the rear of a test slide illustrating the application of a developing solution.

DETAILED DESCRIPTION OF THE INVENTION

The present invention relates to a chromogen-reagent test system which may be utilized in connection with slides, test kits and the like. The present invention will be more fully described in the context of a fecal occult specimen test slide. The principles of the present invention are not, however, restricted to the disclosed form of slide.

Referring now to the Figures, a blank 10 formed for example from paper or cardboard, has a front panel 12, a rear panel 14 and a cover 16. A crease line is provided so that the cover 16 hinges relative to the front panel 12. The cover 16 has a tab 18 which is adapted to pass through a slit 20 in the front panel 12 to lock the cover 16 in a closed position.

The front panel 12 has a plurality of openings 22 therethrough and absorbent paper 24 underlies the openings with the paper between the front and rear panels 12, 14, respectively. The paper 24 may be impregnated or printed with a first reagent such as guaiac.

The rear panel 14 includes a flap 26. The flap 26 is hinged on one side to the rear panel 14 and may be perforated on the other three sides in contact with the rear panel 14 so that upon lifting the flap 26 the connecting material between the flap and the rear panel 14, on three sides thereof, will be severed thus exposing the rear portion of the paper 24.

A portion of the paper 24 includes a control, monitor or indicator area 28 having a positive indicator 30 and a negative indicator 32.

Other details of a slide of the type heretofore described may be understood by reviewing U.S. Pat. No. 4,365,970.

To utilize the slide, the patient opens the front cover 16 and applies a fetal smear or specimen from a portion of the stool onto the paper 24 through the openings 22. The patient then closes the cover 16 so that the tab 18 enters the slit 20 and the slide may be submitted either to the physician or to a laboratory.

The physician or laboratory technician opens the rear flap 26 and applies a hydrogen peroxide reagent 34, which functions as a developing solution, onto the paper 24 opposite the openings 22. The developing solution is also added to the indicator area 28, specifically over the positive and negative areas 30, 32, respectively.

According to the principles of the present invention, the application of the developing solution may be made to the indicator area first or to the specimen area first. However, the application of the developing solution must be substantially closely related, in time, to insure that nothing has intervened which can cause the guaiac paper to lose its sensitivity or alternatively that no additional catalyst could have contacted the guaiac paper. Furthermore, the same developing solution must be used for the specimen areas and for the indicator test areas.

After application of the developing solution, the test results are observed. A negative result on the paper 24 above an opening 22 is indicated by the absence of a color change while a positive test is indicated by the presence of a color change. If guaiac is used the color blue indicates a positive test result.

With respect to the indicator area 28, the positive indicator 30 should change color unless either the guaiac has lost its sensitivity or the hydrogen peroxide has lost its activity. The negative indicator area 32 should remain white, i.e., there should not be any color change, unless the guaiac paper has been subjected to a catalyst other than blood.

If the positive indicator area turns blue and the negative indicator area does not turn blue, then the reagents (guaiac and hydrogen peroxide) of the chromogen system are functioning properly.

According to the principles of the present invention, the positive indicator material should be a substance which preferably is more stable than the hemoglobin in the stool sample with respect to adverse environmental conditions since the present invention has, as its objective, to test the functioning of the two reagents in the chromogen-reagent system, namely, in the case of fecal occult blood testing, the present invention desires to test the efficacy of the guaiac and the hydrogen peroxide.

According to the principles of the present invention, the positive indicator area 30 should include both the guaiac reagent imprinted on the paper or substrate 24, and a substance which will catalyze the hydrogen peroxide reagent to cause the guaiac to change color. Examples of the type of substance which may be used are lead acetate or cupric cyanide.

If lead acetate is selected as the positive indicator, the lead acetate may be prepared as follows. Lead acetate is dissolved in hot glycerol to yield a concentration of eight grams per 100 milliliters. Mixing is necessary as part of this dissolution to solublize the lead acetate and the heated glycerol is preferred to aid the dissolution. The lead acetate-glycerol solution is combined with an O.P. water based varnish (Inmont Printing Inc.) at a ratio by volume of one part lead acetate-glycerol to 9 parts varnish. This mixture may thereafter be printed on the guaiac impregnated slide by standard offset printing equipment.

The second alternative suggested herein is cupric cyanide. To prepare the cupric cyanide, the first step is to dissolve copper sulfate pentahydrate in water to yield 4 grams per 100 milliliters concentration. Potassium cyanide is dissolved in the same container in which the copper sulfate pentahydrate was previously dissolved to yield an 8.0 grams per 100 milliliter concentration. The copper sulfate and potassium cyanide react to yield cupric cyanide. The cupric cyanide is combined with a water based O.P. varnish at a ratio of one part cupric cyanide to 9 parts varnish. Then with standard offset printing equipment the cupric cyanide may be printed on the guaiac-impregnated paper.

For each of the above substances, binders or thickeners conventionally used in offset printing may be employed if desirable to facilitate printability. An example is clay white.

At present the lead acetate is preferred for the positive indicator since it appears to have the greatest stability-the lead acetate does not react like hemoglobin to adverse environmental conditions. The positive indicator material may be hemoglobin- free.

The negative indicator 32, of course, is paper impregnated and guaiac alone.

As distinguished from the controls or monitors described in the aforementioned Lawrence et al patent, it must be emphasized that the objective of the present invention is to determine if the chromogen-reagent test system is functioning properly, i.e., to determine if the guaiac has lost its sensitivity, to determine if the guaiac has been improperly catalyzed, and to determine if the hydrogen peroxide has lost its activity. It is not the function of the present invention to determine whether or not any blood present in the stool has been subjected to adverse environmental conditions causing the blood to lose its activity.

Accordingly, the positive indicator material may be applied to the guaiac impregnated paper at any time before the hydrogen peroxide is to be applied. However, for manufacturing convenience, the positive indicator material is applied during manufacture of the test slide.

The foregoing is a complete description of the present invention. The invention, however, should be limited only by the following claims.

What is claimed is:

1. An occult blood specimen test system including a sheet member carrying a first reagent which has a color change reaction in response to the presence of a second reagent and blood, and an indicator area defined as a portion of the sheet member for indicating the functionality of the system, said indicator area including a positive indicator region for indicating the functionality of said reagents and a negative indicator region for indicating if said first reagent has been improperly catalyzed, said positive indicator region including the first reagent and a catalyst for causing the color change reaction of the first reagent in response to the presence of the second reagent, said catalyst further characterized in not reacting to adverse environmental conditions in a manner similar to hemoglobin which adverse environmental conditions would cause the first reagent to lose the ability to change color in the presence of blood and the second reagent.

2. The invention as defined in claim 1 wherein the catalyst is more stable than hemoglobin.

3. The invention as defined in claim 1 wherein the catalyst is selected from the group consisting of lead acetate and cupric cyanide.

4. The invention as defined in claim 1 wherein the sheet member is part of a test slide.

5. The invention as defined in claim 1 wherein the first reagent is guaiac.

6. A method for detecting occult blood using a receiving sheet having a specimen area and a positive indicator area, the specimen area having a reagent which undergoes a color change in the presence of blood and a developing substance, the positive indicator area including a reagent and a catalyst; the catalyst not reacting to adverse environmental conditions in a manner similar to hemoglobin; contacting the specimen area with a fecal specimen and with a developing substance thus causing the reagent in the specimen area to undergo a color change if blood is present in the specimen and if the reagent and developing substance have maintained their lability; applying the developing substance to the positive indicator area at a substantially closely related time to the step of contacting the developing substance to the specimen area; the positive indicator area for indicating the proper functioning of the reagent and the developing substance, and determining, subsequent to the application of the developing substance to the positive test area whether the positive test area has undergone a color change.

7. The method of claim 6 wherein the receiving sheet further includes a negative test area for indicating if the sheet has been subjected to contamination and a reagent, the negative test area to remain free of color change if the specimen sheet has been free of contamination; applying the developing substance to the negative test area; and determining whether the negative test area has undergone a color change.

8. The invention as defined in claim 6 wherein the catalyst is more stable than hemoglobin.

9. The invention as defined in claim 6 wherein the catalyst is selected from the group consisting of lead acetate and cupric cyanide.

10. The invention as defined in claim 6 wherein the receiving sheet is part of a test slide.

11. The invention as defined in claim 6 wherein the first reagent is guaiac.

\* \* \* \* \*